United States Patent [19]
Crespi et al.

[11] Patent Number: 5,935,829
[45] Date of Patent: *Aug. 10, 1999

[54] MUTATION ASSAYS INVOLVING BLOOD CELLS THAT METABOLIZE TOXIC SUBSTANCES

[75] Inventors: Charles L. Crespi, Marblehead; William G. Thilly, Winchester, both of Mass.

[73] Assignee: Massachusetts Institute of Technology, Cambridge, Mass.

[ * ] Notice: This patent is subject to a terminal disclaimer.

[21] Appl. No.: 07/817,971

[22] Filed: Jan. 6, 1992

Related U.S. Application Data

[63] Continuation of application No. 07/427,741, Oct. 27, 1989, abandoned, which is a continuation-in-part of application No. 06/745,898, Jun. 18, 1985, abandoned, which is a continuation of application No. 06/399,851, Jul. 19, 1982, Pat. No. 4,532,204.

[51] Int. Cl.$^6$ .............................. C12N 15/00; C12N 5/08
[52] U.S. Cl. ........................ 435/172.1; 435/372; 435/375
[58] Field of Search .................................. 435/29, 32, 34, 435/172, 240, 241, 948, 172.1, 372, 375

[56] References Cited

U.S. PATENT DOCUMENTS 4,302,535  11/1981  Skopek et al. ................................ 435/6
4,532,204   7/1985  Crespi et al. ............................. 435/29

OTHER PUBLICATIONS

Freedman, H.J. et al., *Cancer Res.* 39:4605–4611 (1979).
Freedman, H.J. et al., *Cancer Res.* 39:4612–4619 (1979).
Tong, C. and Williams, G.M., *Mutagen Res.* 58:339–352 (1978).
Tong, C. and Williams, G.M., *Mutation Res.* 74:1–9 (1980).
Crespi, C. "Xenobiotic Metabolism and Mutation in Diploid Human Lymphoblasts" Ph.D. thesis received by the Library of Massachusetts Institute of Technology on Jul. 30, 1982.
Tong et al., *Mutation Res.* 130:53 (1984).
Gurtoo, H.L. et al., *Cancer Res.* 35:1235–1243 (1975).

*Primary Examiner*—John L. LeGuyader
*Attorney, Agent, or Firm*—Giulio A. DeConti, Jr.; Elizabeth A. Hanley; Lahive & Cockfield, LLP

[57] ABSTRACT

The present invention pertains to a line of human blood cells which have high levels of oxidative activity (such as oxygenase, oxidase, peroxidase, and hydroxylase activity). Such cells grow in suspension culture, and are useful to determine the mutagenicity of xenobiotic substances that are metabolized into toxic or mutagenic substances. The invention also includes mutation assays using these cells, and other cells with similar characteristics.

13 Claims, 2 Drawing Sheets

MUTATION ASSAYS INVOLVING BLOOD CELLS THAT METABOLIZE TOXIC SUBSTANCES

This application is a continuation of application Ser. No. 07/427,741 filed Oct. 27, 1989, now abandoned, which is a continuation-in-part of U.S. Ser. No. 06/745,898 filed Jun. 18, 1985, now abandoned, which is a continuation of U.S. Ser. No. 06/399,851 filed Jul. 19, 1982 now U.S. Pat. No. 4,532,204.

GOVERNMENT INTEREST

The invention described herein was made in the course of or under grants from the U.S. Department of Energy and the National Institute for Environmental Health Sciences.

TECHNICAL FIELD

This invention is in the fields of biochemistry and toxicology.

BACKGROUND ART

Human beings are exposed to a wide variety of substances and processes that are known to be, or are suspected of being, mutagenic. Such exposure may result from a wide variety of sources, including toxic wastes, technologically innovative products, and byproducts of common substances. To help safe-guard society from mutagenic agents, it is necessary to measure the ability of an agent to create or promote alterations in the genetic composition and reproduction of cells and animals. Mutagenicity assays allow for such measurements in laboratories.

Mutagenicity assays typically are conducted by exposing a cell culture to a substance or process that is suspected of being mutagenic. After the exposure of the suspected mutagen is terminated, the culture normally is allowed to grow for a period of time necessary to allow the mutant phenotype to be expressed, called a "phenotypic expression period;" see, for example, U.S. Pat. No. 4,066,510 (Thilly, 1978). The mutant frequency of the exposed culture is then compared with a control culture to determine whether the mutagen exposure induced a higher frequency of genetic change.

Humans suffer from three distinct forms of genetic change: (a) having an abnormal number of chromosomes, (b) having an abnormal structure of one or more chromosomes, (c) having an abnormal sequence in the DNA that constitutes the genetic material of the chromosomes[1].

Abnormalities of chromosome number and structure can often be detected by direct microscopic observation of condensed chromosomes of cells in mitosis. Abnormalities in DNA sequence usually are not micro-scopically detectable, and require indirect means of detection known generally as "gene locus mutation assays."

The terms "mutation assay" or "mutagenicity assay" are used interchangeably herein to include assays which detect any type of genetic change, such as change in chromosomal number or structure, orchange in gene locus.

Genes which encode the information for making an enzyme or protein catalyst are especially useful in mutation assays. Cells carrying only one copy of such a gene can lose the ability to make the enzyme through a single mutation in that gene. Genes located on the sex chromosomes (x and y) are present in only one active copy per cell. Genes located on autosomes are normally present in two copies per cell. It is sometimes possible to select a heterozygote, a cell with only one functional copy of an autosomal gene [2].

The presence or absence of an enzyme within cells may be determined by adding a "selective agent" to the nutrient solution in which the culture is growing so that only cells without the enzyme can grow. The term "selective agent" has been extensively described and is understood by those skilled in the art. Many selective agents are structurally similar to non-toxic molecules that are metabolized by the cell. For example, 6-thioguanine (6-TG) is a toxic analog of guanine; the structure of each is shown below.

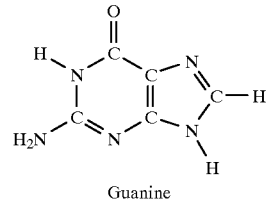

Guanine

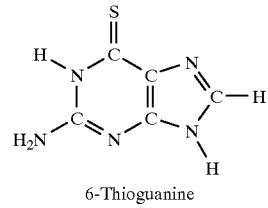

6-Thioguanine

A toxic analog such as 6-TG will be utilized by a cell only if a certain enzyme is present in the cell. Cells which lack that particular enzyme will survive the exposure to the toxic analog. Cells which possess the enzyme in normal amounts will be killed by the toxic analog. In this way, cells which lack certain enzymes can be selected.

Mutation assays have been performed using a number of selective agents of this nature, including the following: 6-TG, which kills cells that contain hypoxanthine-guanine-phosphoribosyl transferase (HGPRT) [3]; 8-azaguanine, which kills cells that contain HGPRT [4]; and trifluorodeoxythymidine, which kills cells that contain thymidine kinase [5].

In a typical mutation assay, replicate cell cultures are exposed to different concentrations of a test chemical (a suspected or known mutagen). A control culture is handled identically in all aspects except it is not exposed to the test chemical. After recovery from the mutagen exposure and phenotypic expression of any newly induced mutations, the relative survival in the presence of the selective agent for each cell culture is determined. This relative survival frequency (the number of cells in the cell culture which grow to form colonies in the presence of the selective agent, divided by the number of cells capable of forming colonies) is called the mutant fraction. A significant increase in mutant fraction indicates that the test chemical was mutagenic.

Many such assays involve the cells of bacteria and other lower organisms, and mice and other small mammals. However, the results of such experiments cannot always be extrapolated to determine the mutagenicity of a substance or process when exposed to human cells. Therefore, a number of mutagenicity assays have been developed which incorporate cells of human origin, grown in vitro [6].

Various types of cells in humans contain certain enzymes that metabolize various substances called "xenobiotics." Xenobiotics are foreign substances which do not normally exist within humans and are frequently toxic, and therefore must be excreted. When human cells are isolated from an individual and grown in long term cell culture, the cells tend to lose the ability to metabolize xenobiotics. If it is desired to conduct a mutagenicity assay that involves one or more xenobiotic substances, then it frequently is necessary to add to the cell cultures an exogenous xenobiotic metabolizing system. These systems commonly include tissues homogenate or whole cells isolated from an animal. The enzymes which carry out xenobiotic metabolism are exogenous, i.e., they act outside of the human cells being assayed. By contrast, "endogenous" enzymes are created, and normally act, within the cells being assayed. The most common source of exogenous xenobiotic-metabolizing enzymes is rodent (mouse or rat) liver. These enzymes are usually prepared by removing the liver from the animal, homogenizing the liver tissue, and centrifuging the homogenate to remove the relatively dense material. The resulting supernatant is referred to as post-roitochondrial supernatant (PMS) [7].

Many types of normal tissues, and PMS preparations from such tissues, are capable of xenobiotic metabolism. Such metabolism tends to occur at relatively high rates in certain types of cells, such as liver cells and bronchial cells. The normal function of this metabolism is to convert non-polar (lipophilic) xenobiotic compounds to more polar, water-soluble forms which can be more easily excreted by the body. Occasionally during this process, chemically reactive metabolites such as epoxides are produced. Some of the reactive metabolites can cause mutations. The level of several xenobiotic metabolizing activities can be increased (or induced) by treatment with certain xenobiotics, such as benzo($\alpha$)pyrene and beta-naphthoflavone.

Several types of enzymatic activities are capable of converting various xenobiotic compounds into potentially mutagenic metabolites. Several activities which are of particular interest herein are designated as oxygenase, peroxidase, oxidase and hydroxylase activities. Those terms are sometimes times used improperly and inconsistently in scientific articles, and various reference works [8] should be referred to for exact definitions used by those skilled in the art. In general, these activities usually act upon substrate molecules by adding oxygen atoms or oxygen-containing moieties, or by withdrawing electrons. For convenience, the term "oxidative" is used herein to include oxygenase, peroxidase, oxidase, and hydroxylase activity.

If a hydroxylase enzyme acts upon an aryl hydrocarbon substrate molecule, such activity may be referred to as "aryl hydrocarbon hydroxylase" (AHH) activity. AHH activity can produce phenols and epoxides from polynuclear compounds, as shown by the example reactions set forth in FIG. 3. In the reactions shown in FIG. 3, double bonds are assigned to specific locations so that the bonding reactions are compatible. However, in most aromatic compounds, the electrons are in resonant configurations.

An enzyme which can act upon a variety of substrate molecules is commonly called a "mixed function" enzyme.

In their reduced state and in the presence of carbon monoxide, certain mixed function oxidative enzymes absorb light with a wavelength maximum around 450 nanometers (nm). Because of this characteristic, such enzymes are often referred to as "cytochrome P-450" enzymes. These enzymes are present in rodent liver PMS, and are capable of mixed function oxidative activity. Cytochrome P-450 enzymes include several distinct isozymes.

The use of PMS preparation, or other sources of exogenous enzymes, in a mutation assay involving human or other cells, may lead to several problems. Such problems include:

1. Enzymes from different species of animals are likely to differ in their chemical makeup and metabolic processes. This leads to uncontrolled variations and uncertainties in the biochemical reaction.

2. Exogenous enzymes usually do not enter the cells; instead, they normally perform their specialized functions on molecules that are outside of cells. This differs from the normal function of these enzymes, which normally act within cells.

3. Exogenous enzymes are likely to create different metabolities compared to endogenous enzymes. For example, an oxygen atom might be bonded to any of several different carbon atoms within an aromatic molecule to create numerous different types of epoxides or phenols. The epoxides and phenols that result from varying enzymes may vary structurally, and may have differing characteristics and biochemical functions.

4. The preparation and addition of exogenous enzymes requires delay and expense. Also, the addition of exogenous enzymes must be carefully controlled in regard to numerous parameters, such as pH and concentration, and steps must be taken to ensure sterility.

5. Homogenate preparations typically contain numerous enzymes and other biochemicals in addition to the specific enzymes desired. Such impurities can lead to reactions that differ from or interfere with the desired reaction. In addition, such impurities may exert toxic effects.

Certain cells are available which are known to possess relatively high levels of endogenous oxygenase activity [9]. However, such cells tend to suffer from various problems when used in mutagenicity assays. Those problems include:

1. Many of the cells are not of human origin.

2. Many of the cells are not diploid, i.e., they often possess an abnormal number (more or less than two copies) of some chromosomes. Such cells tend to be genetically unstable, which interferes with accurate analysis of mutagenicity assay results.

3. Such cells tend to grow poorly in culture, for reasons which include slow growth rates, poor colony forming efficiency, and limitations on the number of generations that can be grown in culture.

4. Such cells may contain various types of contamination, such as mycoplasma, which interfere with accurate measurement of mutation.

5. Many such cells lines are non-homogeneous, i.e., they contain subpopulations with characteristics that differ from the remainder of the cells. Such subpopulations may contain lower levels of oxidative activity, which may lead to selective advantages during mutagenicity assays that involve relatively toxic concentrations of suspected mutagens. Such subpopulations interfere with accurate analysis of mutation.

6. Most cells which contain endogenous oxidative activity, such as certain types of cells from the liver or respiratory tract, are anchorage-dependent cells. Anchoraae-dependent cells proliferate poorly unless they are allowed to contact a solid surface, such as a microcarrier bead or the wall of a culture flask or roller bottle. This characteristic requires special culturing techniques which increase the time, effort, and expense required to grow such cells. By contrast, cells which are not anchorage-dependent, such as lymphoblasts and other blood cells, can grow in suspension cultures, which are normally stirred to prevent the cells from settling to the bottom of the culture medium. Such cells can usually be Frown with less effort and expense than anchorage-dependent cells. In addition, it is easier to obtain samples of blood cells than to obtain samples of anchorage-dependent cells.

DISCLOSURE OF THE INVENTION

This invention relates to mutagenicity assays involving human cells, including human lymphoblast cells. As an example, the Applicants have discovered, isolated and purified a new line of human cells, designated as "AHH-1" cells, that exhibit high levels of oxidative activity, including aryl hydrocarbon hydroxylase (AHH) activity. This cell line also has other very useful aspects, including: (1) rapid growth rate and high cloning efficiency; (2) the absence of mycoplasma; (3) the ability to grow in suspension; and (4) a stable diploid genome. A deposit of this new cell line has been made with the American Type Culture Collection (ATCC), and has been assigned the following accession number: CRL8146.

In addition, by demonstrating that human cells capable of growth in suspension are capable of oxidative metabolism of xenobiotic substances, this invention has created new methods of conducting mutagenicity assays. It can be anticipated that, through diligent search and improved methods of cell culturing, other cell types or lines capable of oxidative xenobiotic metabolism may be isolated. For example, blood may be extracted from a patient or donor (animal or human) and cells within the blood sample with sufficiently high levels of oxidative activity may be identified, isolated and cultured. Such cells can be utilized to conduct mutagenicity assays as disclosed herein. It is also possible to study numerous donors and characterize the susceptibility of different individuals to chemically-induced genetic change.

BEST MODE FOR CARRYING OUT THE INVENTION

THE AHH-1 CELL LINE

One embodiment of this invention comprises an isolated and purified line of human cells, designated as AHH-1 cells, which possesses high levels of mixed function oxidative (including hydroxylase) activity. This cell line was derived from a culture of lymphoblast cells supplied by the Roswell Park Memorial Institute, designated as RPMI-1788 cells. This cell line was selected because it had been shown to contain some degree of basal and inducible AHH activity [10]. It was characterized by the Applicants and found to have the following properties:

1. Contamination with approximately 100 to 200 mycoplasma organisms per cell. In general, mycoplasma are small pleomorphic bacterial cells which do not possess cell walls. They are parasitic and possibly pathogenic [11].

2. Cloning efficiency in 96-well microtiter plates of approximately 20% efficiency when grown in RPMI 1640 cell culture medium with 10% horse serum supplement.

The Applicants successfully eliminated the mycoplasma contamination by growing RPMI-1788 cells in a stirred culture that was exposed to 200 µg/ml gentamycln and 100 µg/ml kanamycin simultaneously. These concentrations permitted cell growth of about 80 to 90% compared to antibiotic-free medium. The exposed culture was grown for 10 generations, which correlates to about a 1000-fold increase in the cell population. This degree of proliferation was chosen because it was expected to decrease the degree of contamination to less than one mycoplasma per cell; in addition, the relatively short duration of drug exposure (about 7 days) reduced the possibility of selecting a line of antibiotic-resistant mycoplasma. After this exposure, the cells were plated in microtiter plates at a low density, about 0.2 cells per well, to increase the probability that some or most of the result- ing colonies would be free of mycoplasma contamination. Forty-seven colonies were grown in this manner, and one colony was determined to be of particular interest.

Figure 1:
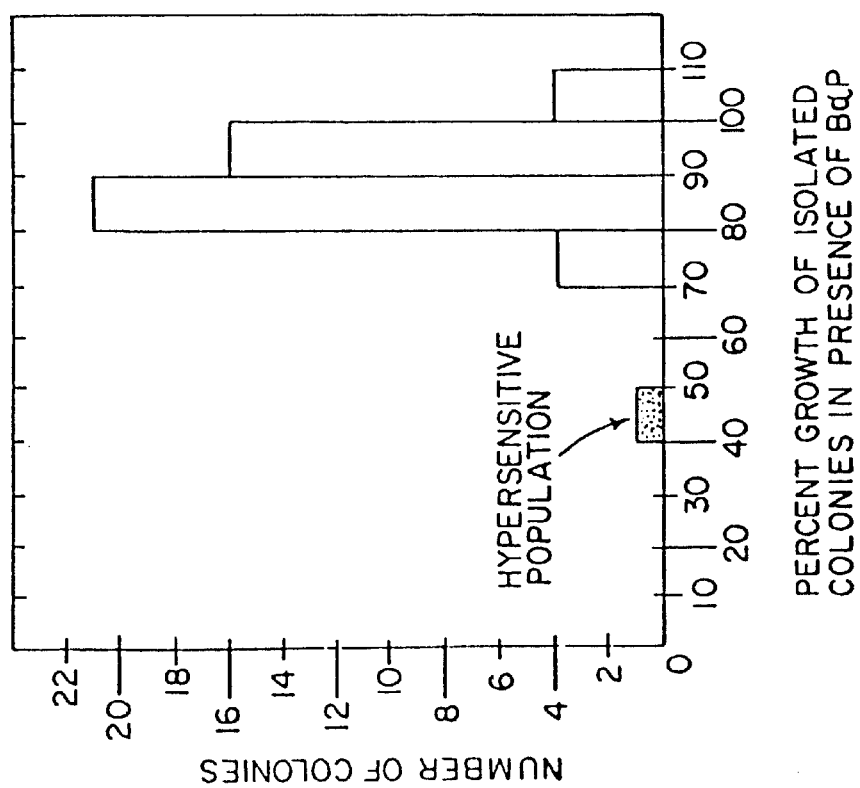
FIG. 1 indicates the growth characteristics of 47 isolated colonies of cells derived from RPMI 1788 cells when exposed to benzo(α)pyrene. The shaded area represents a hypersensitive colony which was the pro-genitor of the AHH-1 cell line.
Figure 3:
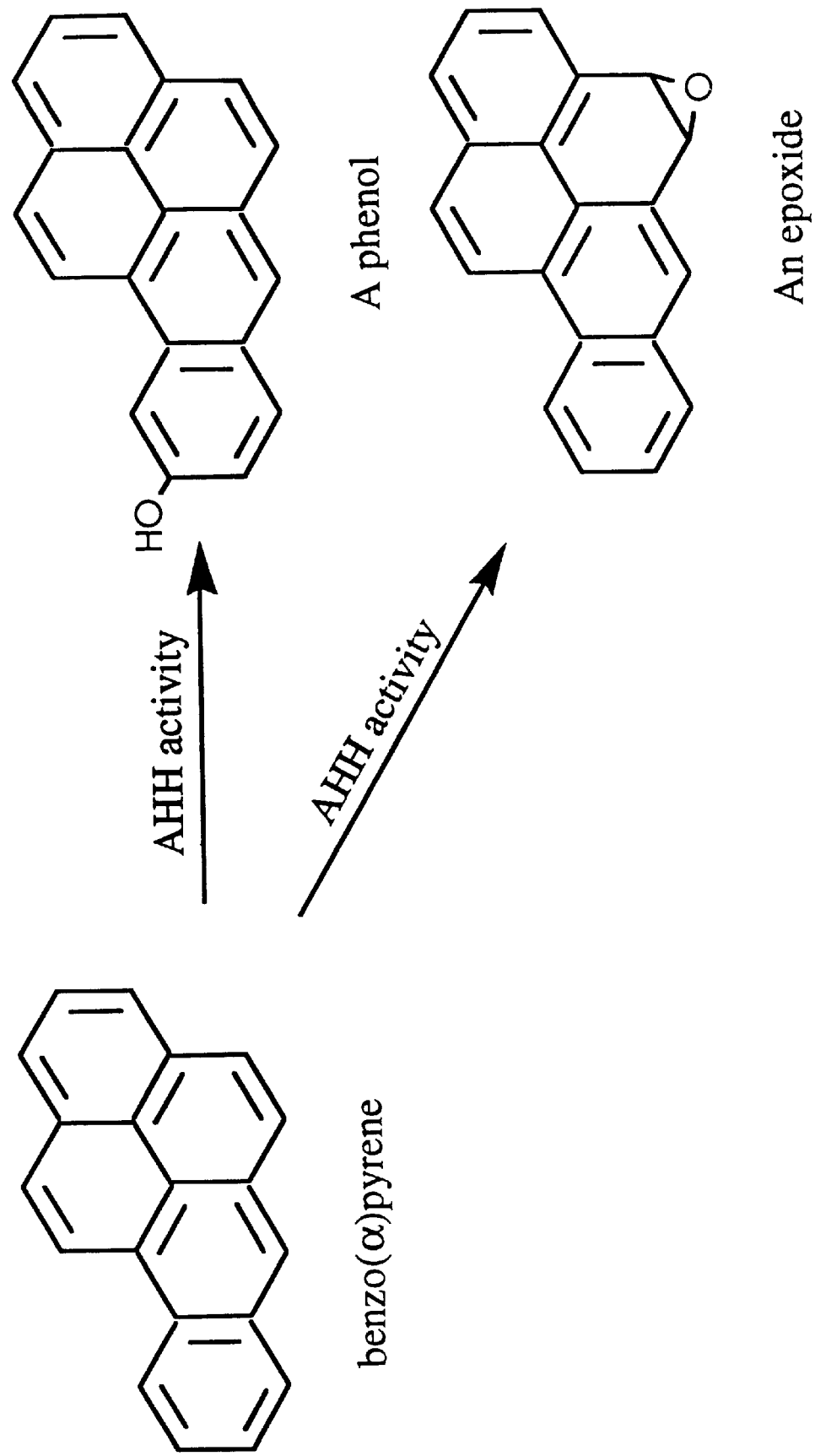
FIG. 3 depicts the some reactions by which AHH activity can produce phenols and epoxides from polynuclear compounds.

The 47 colonies of RPMI-1788 cells that were treated as described above were all tested for AHH activity by exposing them to 40 µM benzo(α)pyrene (BaP) for 48 hours. Although BaP at that concentration -is not highly cytotoxic, it may be metabolized by AHH activity into several types of phenols, diols, and epoxides that are highly cytotoxic. Therefore, a high incidence of cell mortality upon exposure to BaP indicates that the exposed culture contains a relatively high level of AHH activity. When the 47 cultures were exposed to BaP, one culture exhibited a very high mortality rate compared to the other cultures, as shown in FIG. 1. This cell line was designated as the AHH-1 line.

The AHH-1 cell line was further purified by two more clonings in gentamycin-kanamycin medium. AHH-1 cells were tested for mycoplasma and found to be free of contamination.

The AHH-1 cell line was tested to assess its suitability for use in mutagenicity assays by exposing cultures of AHH-1 cells to various chemical agents that are known to be mutagens. These mutagenic agents include ethyl methanesulfonate and ICR-191. Both of these agents are direct-acting mutagens; they do not need to be metabolized in order to become mutagenic.

Table 4 (which is described in Example 6) indicates that increasing concentrations of each mutagen induced increasing incidences of mutation, as indicated by the number of cells that become resistant to 6-TG, a selective agent. This behavior confirms that the AHH-1 cell line is a suitable cell line to be used in mutagenicity assays. These results also support the exposure and assay procedures used by the Applicants.

The AHH-1 cell line has a level of oxidative activity which is sufficiently high to cause a statistically significant degree of mutation (in the absence of exogenous oxidative activity) if a culture is contacted with a chemical which is known to require oxidative activation in order to become mutagenic. Such chemicals include benzo(α)-pyrene, aflatoxin $B_1$, 2-acetoaminofluorene, and dimethyl nitrosamine. The phrase "statistically significant degree of mutation" is discussed extensively in the literature [12] and is understood by those skilled in the art. It should be noted that there are several ways of defining "statistical significance," involving parameters such as confidence limits, standard deviations, percentiles, etc. In addition, a boundary (such as a 95% confidence limit, as used by the Applicants) between significant and not-significant is usually chosen arbitrarily or by convention. The term "statistical significance" is not limited to any particular method of analysis, or to any particular boundary.

The AHH-1 cell line may be grown readily in commercially available culture medium, which may be supplemented by blood serum from various mammalian species. The economically optimal medium and supplementation may be determined through routine experimentation by someone skilled in the art. For example, it has been found that AHH-l cells grow readily in RPMI medium 1640 supplemented by 5% (by volume) horse serum. The AHH-1 cell line is not anchorage-dependent; it can be grown in stirred suspension culture.

One surprising and important advantage of the AHH-1 cell is its high degree of plating efficiency, which indicates the percent of cells that will form clonal colonies when seeded into microtiter plates. The RPMI-1788 cell line, from which the AHH-1 cells were derived, plated with about 20% efficiency in RPMI medium 1640 supplemented with 10% horse serum. In comparison, the AHH-1 cell line plates with about 40 to 80% efficiency in RPMI medium 1640 supplemented by only 5% horse serum. This substantially reduces the cost of assays using AHH-1 cells.

In addition, the AHH-1 cell line has a relatively stable diploid chromosome content. Numerous observa- tions indicate that the large majority of AHH-1 cells have 46 chromosomes.

In addition, the AHH-1 cell line has been shown to be homogeneous, i.e., free of resistant subpopulations that would interfere with accurate analysis of mutagenicity assays involving toxic agents.

The AHH-1 cell line is believed to be a line of cells, rather than a strain of cells, as those terms are commonly used by people skilled in the art. As a cell line, AHH-1 cells are believed to be capable of "immortal reproduction," i.e., reproduction for an unlimited number of generations without substantial loss of reproductive rates. By contrast, the reproductive rates of a cell strain tend to diminish greatly after a substantial number of generations, e.g., about 30 generations, and cell strains often are not able to reproduce beyond some limit, e.g., about 50 generations. It may be possible to cultivate a strain of cells for an unlimited number of generations if all necessary nutrients, growth factors, other biochemicals needed for reproduction are identified and supplied. However, such biochemicals are often expensive, and it is normally cheaper and more convenient to utilize a cell line than a cell strain even if the reproductive constraints can be overcome. For these reasons, the economic value of an immortal cell line normally is superior to the value of a cell strain with identical characteristics.

As used herein, the terms "biologically pure" and "purified" refer to the absence of mycoplasma, bacteria, and other viable microorganisms which would interfere with a particular use of a culture of cells. It is not necessary that a culture be absolutely devoid of all heterogenous organisms in order to qualify as biologically pure. However, in order to qualify as biologically pure, a culture must be the result of human efforts which are intended to isolate the type of cell involved and remove it from other types of cells which normally surround it. A purified cell culture which is mixed with an organism that is innocuous with regard to a desired use of the culture, or which is mixed with a second purified culture that is useful for imparting a desired characteristic to the resulting mixed culture, should be regarded as "purified." Normally, purity is protected and maintained by techniques which are known to those skilled in the art.

The "relevant identifying characteristics" of a cell culture are limited to the characteristics which affect the performance of the culture in a specific use. For example, in the use of an AHH-1 cell in a typical mutagenicity assay, the relevant characteristics of the cell will usually include (1) its origin as a human blood cell, (2) the fact that it has a relatively high plating efficiency, and (3) the fact that it has a high level of oxidative activity. For any given assay, numerous other characteristics may be irrelevant, e.g., the resistance of the culture to a drug that is not essential to the assay. Using techniques known to those skilled in the art, it is possible to create innumerable subclones of any cell culture with varying characteristics, e.g., resistance to selected drugs, a plating efficiency that is slightly below any arbitrarily chosen level, etc. Such variations may amount to improvements in the AHH-1 cell line, which undoubtedly will occur as more skilled researchers gain access to the AHH-1 cell line. However, unless such variations materially alter the performance of such cells when they are used for the purposes contemplated by this invention, then such variations should not be regarded as modifications of the relevant identifying characteristics.

Mutagenicity Assays

In addition to the isolated and purified AHH-1 cell line, this invention comprises mutagenicity assays that involve the AHH-1 cell line, or other cells that grow in suspension and exhibit oxidative activity. These assays are enhanced and rendered more convenient and accurate and less expensive and time-consuming, by the characteristics of the AHH-1 cells or similar cells.

One preferred embodiment of a mutagenicity assay of this invention, utilizing AHH-1 cells as an example, comprises the following steps: (1) dividing a culture of AHH-1 cells into at least two aliquots (prefereably, such assays are performed simultaneously on numerous cultures using each mutagen concentration on two or more cultures); (2) exposing at least one of the aliquots to a suspected mutagen; (3) growing the exposed aliquot and at least one unexposed control aliquot for a phenotypic expression period; (4) contacting all aliquots with a selective agent; (5) determining the survival incidence of cells in each aliquot in the presence of the selective agent; and (6) comparing the survival incidences to obtain an indication of whether the genetic makeup of the cells was altered by exposure to the suspected mutagen.

Assays of this invention may be used to assess the mutagenic effects on AHII-1 cells and similar cells of virtually any substance, process, or combination thereof. The proper concentration and period of exposure to any suspected mutagen may be determined through routine experimentation by someone skilled in the art. For example, a culture of AHH-1 cells or other cells may be divided into numerous cultures, and exposed to different concentrations of a suspected mutagen, or to a given concentration for varying durations, or to a combination of mutagens. Exposure may comprise contact with a chemical, radiation of energy, or any other method of exposure or combination of exposures. The exposed cultures, and unexposed control cultures, may then be assayed by selective agents or other means to assess genetic change.

Numerous types of selective agents may be used in a mutagenicity assay involving AHH-1 cells or similar cells. For example, toxic analogs (such as 6-TG, 8-azaguanine, or trifluorodeoxythymidine, which damage or kill cells that contain certain enzymes) may be used as selective agents in this invention. Cytotoxic drugs, such as methotrexate, which damage or kill cells that do not contain normal or abnormally high levels of certain enzymes, also may be used as selective agents in this invention. Selective agents may also comprise substrates which change color if reacted by certain enzymes. Numerous selective agents are now known or will be discovered through subsequent research. Whether such a selective agent, or combination of selective agents, is suitable for use with AHH-1 cells or similar cells may be determined through routine experimentation. For example, AHH-1 cells may be exposed to a known mutagen such as ethyl methanesulfonate or ICR-191, and subsequently exposed to a potential selective agent to determine whether the selective agent is useful for detecting genetic alterations caused by the known mutagen. The AHH-1 cells and similar cells are likely to prove useful in research to locate and assess the properties of potential selective agents, by simplifying the assay procedures involved in such research.

One embodiment of a mutagenicity assay of this invention comprises pretreating a culture of AHH-1 cells or similar cells with a selective agent prior to exposing the cells to a mutagen. This procedure can be used to increase the accuracy of the mutagenicity assay by killing pre-assay mutants. For example, a culture of AHH-1 cells may be exposed to CHAT (a mixture of cytidine, hypoxanthine, aminopterin, and thymidine) to kill cells that do not contain both HGPRT and thymidine kinase. Normal AHH-1 cells contain both of these enzymes. Pre-assay mutants, which decrease the sensitivity of the assay, are killed before the assay begins. Shortly after the CHAT is removed, the culture is divided into at least two cultures, and at least one of the cultures is exposed to a suspected mutagen. After a phenotypic expression period, all cultures are exposed to a selective agent, such as 6-TG, 8-azaguanine, or 6-mercaptopurine, which kills cells that contain HGPRT. This ensures that the only cells that survive the post-mutagen selective agent are cells that mutated (to inactivate the HGPRT gene) during or shortly after exposure to the suspected mutagen.

Other types of assays, which might not involve selective agents, may also be used to assess genetic change. For example, observation under a light microscope is often used to detect changes in chromosome number or structure. Other techniques, such as flow cytometry, are also being developed to assay genetic change. Such assays are included within the term "mutation assays" as previously defined herein, and are within the scope of this invention.

The use of blood cells or other cells capable of growing in suspension to determine genetic change caused by xenobiotic substances has several very important advantages. It is much easier to extract a blood sample than a tissue sample from a patient or donor. It is also possible to take blood samples from a large population, such as all workers employed in an industrial plant, to determine the potential effects of chemicals on the workers.

As used herein, the term "cell population" includes a plurality of cells with reproductive capability, regardless of whether such cells comprise a line or a strain of cells. The term also applies regardless of the current condition of the cells; for example, a cell population may be actively growing in a suitable culture medium, or it may be frozen or otherwise inactivated for purposes such as storage or shipping.

EXAMPLES

Example 1
Cells and Chemicals Used

RPMI-1788 cells were a gift from Dr. H. L. Gurtoo of Roswell Park Memorial Institute (Buffalo, N.Y.). This cell line was determined to have the following characteristics:

1. Cloning efficiency of about 15 to 20% in microtiter plates when grown in RPMI medium 1640.
2. Contamination with about 100 to 200 mycoplasma per cell.
3. Basal AHH activity of about 0.1 pmole of 3-hydroxy BaP per $10^6$ cells per minute. The quantity of 3-hydroxy BaP was measured by fluorescent intensity activated by a light wavelength of 396 nm and measured at 522 nm using a spectrofluorimeter (Farrand Model Mk-1, Valhalla, N.Y.). This could be induced to about 0.3 pmole of 3-hydroxy BaP per $10^6$ cells per minute.

Except as otherwise specified, all chemicals used were obtained from Sigma Chemical Co. (St. Louis, Mo.). Horse serum and growth medium (RPMI medium 1640) were obtained from Flow Laboratories (McLean, Va.) or GIBCO (Grand Island, N.Y.). CHAT pretreatment was performed using published procedures [12].

Example 2
Growth and Plating Procedures

The cells used were grown in growth medium RPMI 1640. This growth medium was supplemented with various quantities of horse serum or fetal calf serum. Cell growth rates, plating efficiency, and oxidative activity were evaluated as a function of concentration of serum, and it was determined that optimal economic and evaluative results using AHH-1 cells could be obtained by using 5% horse serum.

The cells may be maintained in exponential growth by daily dilution to $2-4\times10^5$ cells/ml. Cell doubling times ranged from 13.5 to 22 hours depending upon culture conditions; faster growth was obtained in stirred culturing conditions than stationary cultures.

The microtiter plating technique [13] involves aliquoting a known number of cells into 96-well microtiter plates. Cells grow in the wells and eventually form macroscopic colonies, typically after 10 to 14 days. The number of colonies is scored using a low-power optical microscope. Poisson statistical methods are used to calculate the number of colony-forming-units per well (cfu/w) by means of the following formula:

$$cfu/w = \ln \frac{\text{number of total wells}}{\text{number of wells without colonies}}$$

Cloning efficiency is determined by aliquoting a known number (from 1 to 5) of cells into each well, and dividing the calculated value of cfu/w by the number of cells aliquoted into each well.

Mutant frequency is determined by aliquoting a known number of cells (up to 20,000) per well in the presence of 6-TG, a selective agent which kills cells that contain HGPRT activity. The plates are incubated for 12 days, and the colonies are scored. The mutant fraction can be calculated according to the following equation:

mutant fraction equals AB/CD, where:
A=# of cfu/w in the presence of 6-TG;
B=# of cells per well in the absence of 6-TG;
C=# of cfu/w in the absence of 6-TG;
D=# of cells per well in the presence of 6-TG, Example 3
Curing of Mycoplasma and Isolation of AHH-1 Cell Line As mentioned in Example 1, the RPMI-1788 cell culture was contaminated with about 100–200 mycoplasma per cell.

To remove these mycoplasma, the cells were grown in growth medium containing 200 ug/ml gentamycin and 100 ug/ml kanamycin. The cells were grown in spinner culture for ten generations, which corresponds to a 1,000-fold increase in cell number. This amount of proliferation was chosen because it was expected to decrease the average number of mycoplasma per cell to less than one. In addition, it was sufficiently brief so that selection for antibiotic resistant mycoplasma was not likely.

After growth of the cells in culture medium with gentamycin and kanamycin, the cells were plated in microtiter plates at a density of about 0.2 cells per well. Colonies were isolated and characterized for BaP-induced growth inhibition. A total of 47 colonies were isolated and contacted with 40 uM BaP. In its normal state, BaP is not highly cytotoxic or mutagenic; however, if metabolized by oxidative activity into one or more epoxides or phenols, the metabolites tend to be toxic and mutagenic. Of the 47 colonies isolated, one was found to be hypersensitive to BaP (see FIG. 1); this indicated abnormally high levels of oxidative activity. This activity as measured by 3OHBaP fluorescence, was determined to be 0.1 to 0.07 pmole 3-OHBaP per $10^6$ cells per minute (basal level), and 1 to 3 pmole 3-OHBaP per $10^6$ cells per minute if induced by contact with 10 uM BaP for 24 hours.

The selected colony was recloned twice at low cell density (0.2 cells per well in culture medium containing gentamycin and kanamycin to insure that the mycoplasma contamination was eliminated. A sample of cells from each generation was exposed to BaP; each sample was found to be hypersensitive to BaP, which indicated that abnormally high levels of oxygenase activity were a stable phenotypic trait of the cell line. A single subclone was chosen because it formed large, homogeneous colonies with relatively high plating efficiency (40%–80%) in microtiter wells. It was designated the "AHH-1" cell line.

Example 4:
Optimization of Mutagenicity Assay Parameters

When applied at relatively high concentrations to a colony of cells, 6-thioguanine (6-TG) causes the cells to clump together, rendering it difficult or impossible for live mutant cells to survive and create colonies. It was found that at concentrations of 5 $\mu$g/ml of 6-TG, only about 2,000 cells per microtiter well could be assayed without clumping. However, when the concentration of 6-TG was reduced to 0.5 $\mu$g/ml, it was found that 20,000 or more cells per microtiter well could be assayed. Subsequent routine work was done using 0.5 $\mu$g/ml of 6-TG.

In order to confirm that mutant varieties of AHH-1 cells behave as true mutants, an independent experiment was performed. A mutant population of AHH-1 cells that were resistant to 6-TG were plated at very low density (about two cells per well). This population was not sensitive to the toxic effects of 6-TG in concentrations up to 5 $\mu$g/ml.

Figure 2:
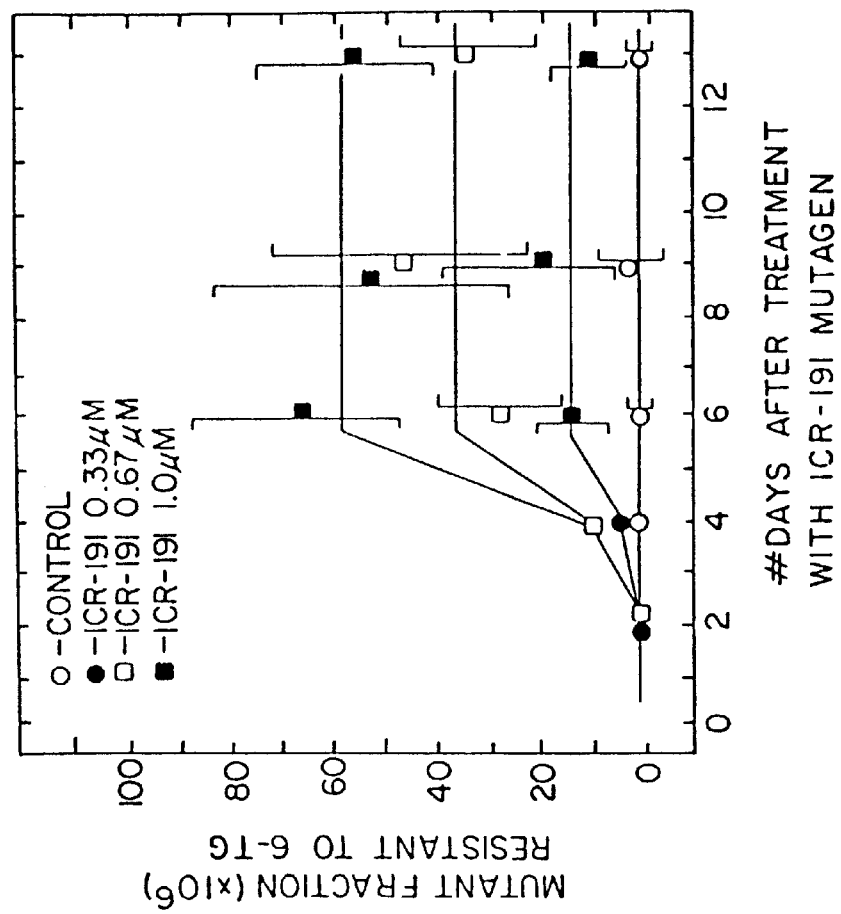
FIG. 2 indicates the mutant fraction induced by treatment of AHH-1 cells with ICR-191,determined by measuring the frequency of resistance to 6-thioguanine.

AHH-1 cell cultures were contacted with ICR-191 (Polysciences Inc, Warrington Pa.) which is a known mutagen comprising an acridine mustard derivative, at varying concentrations ranging up to 1.0 $\mu$M, for 24 hours. The cultures were resuspended in growth medium and allowed to grow. At different times after treatment, the cells were contacted with 6-TG to determine the mutant fraction. The induced mutation was fully expressed within 6 days after contact with ICR-191, and the mutant fraction remained relatively stable for the duration of the experiment, 14 days (see FIG. 2).

Example 5
Tests to Determine Systemic Bias

A mutagenicity assay should give an accurate measure of an induced mutation rate. There are at least three possible processes which may interfere with an accurate evaluation of induced mutation. First, the apparent mutant fraction may be altered by differences in the growth rate for mutant cells and non-mutant ("wild-type") cells under non-selective conditions. For example, if mutant cells grow more rapidly for some reason than wild-type cells, the apparent mutant fraction may be misleadingly high. Second, if mutant cells have plating efficiencies that are different from wild-type cells, the apparent mutant fraction may be misleading. Third, if non-homogeneous subpopulations have a non-mutagenic selective advantage when subjected to toxic selective agents, the apparent mutant fraction may be misleading.

In order to test for systemic bias, AHH-1 cells were contacted with BaP to induce mutation, grown for a phenotypic expression period, and contacted with 6-TG, a selective agent. Seven clones which were resistant to 6-TG, and one "wild-type" AHH-1 cell culture which was not resistant to 6-TG, were isolated and grown in RPMI medium 1640 with 5% horse serum. All seven clones had similar growth rates under nonselective conditions compared to wild-type cells. This indicates that there is no selective pressure for or against the mutant cells due to differential growth rates. In addition, all seven clones were sensitive to CHAT, and grew with comparable growth rates with and without 6-TG present in the growth medium. This indicates that the putative 6-thioguanine resistant colonies observed were also 6-thioguanine resistant, as indicated l)y cell growth measurement.

The inability to grow in CHAT indicates that the colonies did not have enough HGPRT activity to phosphoribosylate hypoxanthine and support cell growth.

The seven clones that were resistant to 6-TG were tested against wild-type cells for plating efficiency, in RPMI medium 1640 with 5% horse serum. As indicated in Table 1, the mutant colonies plated with similar efficiencies with and without 6-TG and with and without 2000 wild type cells per well. This indicates there is no bias due to differential plating efficiency.

TABLE 1

Plating efficiency of clones resistant to 6-TG

| Clone # | Plating Efficiency at 2 cells/well | Plating Efficiency in 5 $\mu$g/ml 6-TG at 2 cells/well | Plating Efficiency with 6-TG & 2000 c/w |
|---|---|---|---|
| BP-3 | 0.22 | 0.24 | 0.23 |
| BP-4 | 0.33 | 0.34 | 0.34 |
| BP-5 | 0.15 | 0.21 | 0.20 |
| BP-6 | 0.33 | 0.26 | 0.34 |
| BP-7 | 0.06 | 0.06 | 0.07 |
| Wild type | 0.25 | <$10^{-3}$ | $10^{-5}$ |

Preferential survival during toxic treatment tested by exposing two sets of cells to varying concentrations of ICR-191. One set comprised AHH-1 cells that were not resistant to 6-TG; the other set comprised AHH-1 cells that had been induced to exhibit 6-TG resistance by contact with ICR-191. A slight difference in survival rate was observed, as indicated in Table 2, but the difference did not reach the level of statistical significance.

TABLE 2

Toxicity of ICR-191 to AHH-1 cells

| ICR-191 Concentration, | Relative Survival | |
|---|---|---|
| μg/ml at 24 hrs. | AHH-1 cells | 6-TG$^r$ AHH-1 cells |
| 0 (control) | 1.00 | 1.00 |
| 0.25 | 0.65 | 0.48 |
| 0.5 | 0.48 | 0.20 |
| 1.0 | 0.13 | 0.14 |

6-TG resistant clones were characterized for AHH activity by measuring the rate of production of 3-OH benzopyrene, a fluorescent metabolite of BaP which is created by AHH activity. Basal AHH activity for uninduced AulH-1 cells was determined, as well as AHH activity induced by exposure to 10 μM BaP for 24 hours. The 6-TG resistant clones contain AHH activity which is comparable to AHH activity of uninduced AHH-1 cells, as indicated by the results in Table 3.

TABLE 3

AHH Activity (pmole 3OHBP/10$^6$ cells/minute)
AHH-1 Cells Resistant to 6-TG

| Clone # | Basal AHH Activity | AHH Activity Induced by B(α)P |
|---|---|---|
| BP-1 | 0.20 | 1.64 |
| BP-2 | 0.28 | 2.36 |
| BP-3 | 0.28 | 1.88 |
| BP-4 | 0.16 | 2.76 |
| BP-5 | 0.12 | 0.72 |
| BP-6 | 0.16 | 1.88 |
| BP-7 | 0.28 | 1.84 |
| Wild type | 0.28 | 2.04 |
| Mean TG$^R$ | 0.21 | 1.87 |

Example 6
Mutation Assays Using Direct-Acting Mutagens

AHH-1 cells were tested for mutation using two substances which are known to induce mutation: ethyl methanesulfonate (EMS) and ICR-191.

Stock cultures of AHH-1 cells were grown in plastic tissue culture flasks and diluted daily to 4×10$^5$ cells per ml. Prior to mutagen treatment, pre-existing mutants in the population were eliminated by a 48 hour treatment with CHAT (deoxycytidine, 1×10$^{-5}$M; hypoxanthine, 2×10$^{-4}$M; aminopterin, 2×10$^{-7}$M; and thymidine, 1.75×10$^{-5}$M). Cells were then centrifuged (1000×g for 5 minutes) and resuspended in medium plus THC (CHAT without the aminopterin). The THC treatment was utilized to aid the cells in recovering from the toxic effects of the aminopterin. THC was gradually removed by normal dilutions due to cell growth. Culture volumes were scaled-up to prepare the desired number of cells for mutation measurement. Two days after the addition of THC the cellular oxidative activity was induced (if desired) by the addition of 1×10$^{-5}$M beta-naphthoflavone (BNF) in dimethyl sulfoxide (DMSO); the final DMSO concentration was 0.1%. Three days after the addition of THC, the BNF (if present) was removed by cell centrifugation (twice at 1000×g for 5 minutes). The cells were diluted to 1.5×10$^5$ cells per ml (48 hour mutagen treatment) or 4×10$^5$ cells per ml (24 hour mutagen treatment), and aliquotted into replicate 150 cm$^2$ tissue culture flasks (100 ml per flask). Mutagen was then added, dissolved in DMSO. The final DMSO concentration was kept constant within an experiment and never exceeded 0.3%. DMSO only was added to the negative control cultures and 10 μM BP was used as a positive control. All mutagen concentrations were tested in duplicate. Cultures were incubated with the mutagen for the desired length of time (24 or 48 hours), cell concentrations were determined, and 4×10$^7$ cells were centrifuged and resuspended in 100 ml of fresh medium in a new 150 cm$^2$ tissue culture flask. During the phenotypic expression period (6 days), cell concentration was determined daily and the culture was diluted each day to 4×10$^5$ cells per ml.

6-Thioguanine-resistant fraction was measured by a microwell plating technique which has been published [13]. AHH-1 cells were plated at 20,000 cells per well in the presence of 0.5 μg per ml 6TG and 2 cells per well in the absence of 6TG. Plates were incubated at 37° C. in a humidified 5% CO$_2$ incubator for 14 days. The plates were then scored for the presence or absence of colonies in individual cells and the mutant fraction and confidence interval computed.

The results are displayed in Table 4. These results are comparable to the mutagenic effects of the same chemicals acting upon human lymphoblast cells that do not possess abnormally high levels of AHH activity [14].

TABLE 4

Mutation of AHH-1 Cells in Direct-Acting Mutagens

| MUTAGEN | CONC. × Time(hours) | RELATIVE SURVIVAL | MUTANT FRACTION × 10$^6$ MEAN ± STD.DEV. |
|---|---|---|---|
| CONTROL | DMSO solvent only | 1.00 | 1.9 ± 0.4 |
| EMS | 59 μM × 24 | 0.48 | 6.3 ± 1.3 |
| EMS | 100 μM × 24 | 0.36 | 20 ± 5 |
| CONTROL | DMSO solvent only | 1.00 | 1.6 ± 0.5 |
| ICR-191 | 0.63 μM × 24 | 0.65 | 62 ± 11 |
| ICR-191 | 1.25 μM × 24 | 0.48 | 116 ± 17 |
| ICR-191 | 2.5 μM × 24 | 0.13 | 147 ± 28 |

Example 7
Mutation Assays Involving Indirect-Acting Mutagens

AHH-1 cells were tested for induced mutation using the procedures described in Example 6, by contacting them with the following substances: 2-acetoaminofluorene (2AAF), aflatoxin-B$_1$ (AFB), benzo(a)pyrene (BP), cyclopenteno(c,d)pyrene (CEPE), dimethylnitrosamine (DMN), fluoranthene (Fla), lasiocarpine (LSCP), 1-methylphenanthrene (1MP), perylene (Per). These substances are not substantially mutagenic in their original form; however, if these substances are metabolized by oxidative activity, the metabolites are mutagenic, as has been demonstrated using conventional mutation assays with rat liver homogenate. The exception to this is perylene, which is not a mutagen for human cells [15].

Some of the cells were pretreated to induce AHH activity, by contact with 10 μM beta-naphtho-flavone (BNF) for 24 hours. The cells were centrifuged twice to remove the BNF before the mutagen was added. B(α)P and cyclopenteno(c,d)pyrene (CEPE) are also inducers.

The results, summarized in Table 5, indicate that all of the indirect-acting mutagens (i.e., all of the substances listed except for perylene, which is not a mutagen for human cells) exert a substantial mutagenic effect on AHH-1 cells. Except for fluoranthene, all of the substances tested resulted in mutagenic effects that equal or exceed the 99% confidence limit determined by statistical analyses of the control cultures. This value corresponds with a mutant fraction greater than or equal to $4.8\times10^{-6}$. The mutagenic effects of fluoranthene are being studied further.

TABLE 5

Mutation of AHH-1 Cells by Indirect-Acting Mutagens

| MUTAGEN | Conc. × Time(hours) | INDUCTION | RELATIVE SURVIVAL | MUTANT FRACTION × $10^6$ MEAN ± STD.DEV. |
|---|---|---|---|---|
| Control | DMSO solv. only | None | 1.00 | 1.6 ± 0.5 |
| Benzo (α) - pyrene | 0.3 μM × 24 | BP | 0.87 | 3.4 ± 0.5 |
| " | 1 μM × 24 | BP | 1.02 | 4.9 ± 0.9 |
| " | 3 μM × 24 | BP | 0.74 | 6.1 ± 1 |
| " | 10 μM × 24 | BP | 0.82 | 12.7 ± 1.5 |
| " | 30 μM × 24 | BP | 0.75 | 18.2 ± 2.1 |
| CONTROL | DMSO SOLV. only | None | 1.00 | 2.1 ± .0.5 |
| DMN | 5 mM × 48 | " | 0.98 | 3.5 ± 0.7 |
| DMN | 14 mM × 48 | " | 0.92 | 3.5 ± 0.7 |
| DMN | 28 mM × 48 | " | 0.81 | 4.1 ± 1.3 |
| CONTROL | DMSO solv. only | BNF | 1.00 | 3.2 ± 0.6 |
| DMN | 5 mM × 48 | " | 1.12 | 4.0 ± 0.7 |
| DMN | 14 mM × 48 | " | 1.00 | 8.0 ± 2.0 |
| DMN | 28 mM × 48 | " | 0.87 | 8.6 ± 2.1 |
| CONTROL | DMSO solv. only | CEPE | 1.00 | 2.4 ± 0.6 |
| CEPE | 1 μM × 48 | " | 0.61 | 71 ± 6 |
| CEPE | 3 μM × 48 | " | 0.63 | 78 ± 9 |
| CEPE | 10 μM × 48 | " | 0.59 | 22 ± 2 |
| CEPE | 25 μM × 4.8 | CEPE | 0.54 | 34 ± 4 |
| CONTROL | DMSO solv. only | CEPE & BNF | 1.00 | 0.8 ± 0.3 |
| CEPE | 25 μM × 48 | " | 0.34 | 74 ± 7 |
| CEPE | 50 μM × 48 | " | 0.27 | 64 ± 7 |
| CONTROL | DMSO solv. only | None | 1.00 | 0.7 ± 0.3 |
| LSCP | 100 μM × 48 | " | 1.30 | 5.4 ± 0.6 |
| LSCP | 300 μM × 48 | " | 0.89 | 6.2 ± 1.3 |
| LSCP | 600 μM × 48 | " | 0.82 | 6.0 ± 1.4 |
| control | DMSO solv. only | BNF | 1.00 | 2.8 ± 0.7 |
| LSCP | 10 μM × 48 | " | 1.03 | 3.9 ± 1 |
| LSCP | 100 μM × 48 | " | 0.91 | 4.3 ± 1 |
| LSCP | 300 μM × 48 | " | 0.81 | 12.7 ± 2.1 |
| control | DMSO solv. only | None | 1.00 | 1.1 ± 0.4 |
| 1MP | 25 μM × 48 | " | 0.54 | 4.4 ± 1.2 |
| 1MP | 50 μM × 48 | " | 0.38 | 4.1 ± 1.2 |
| 1MP | 100 μM × 48 | " | 0.31 | 7.8 ± 1.1 |
| control | DMSO solv. only | BNF | 1.00 | 2.0 ± 0.5 |
| 1MP | 25 μM × 48 | " | 0.47 | 3.6 ± 1.2 |
| 1MP | 50 μM × 48 | " | 0.35 | 8.9 ± 1.5 |
| 1MP | 100 μM × 48 | " | 0.29 | 7.8 ± 1.4 |
| CONTROL | DMSO solv. only | None | 1.00 | 2.4 ± 0.6 |
| AFB | 6.8 μM × 48 | " | 0.56 | 27 ± 3 |
| AFB | 13.6 μM × 48 | " | 0.45 | 20 ± 2.5 |
| AFB | 20.4 μM × 48 | " | 0.36 | 35 ± 4 |
| CONTROL | DMSO solv. only | BNF | 1.00 | 4.8 ± 0.9 |
| AFB | 6.8 μM × 48 | " | 0.52 | 17 ± 2 |
| AFB | 13.6 μM × 48 | " | 0.43 | 20 ± 2.5 |
| AFB | 20.4 μM × 48 | " | 0.35 | 25 ± 2.7 |
| control | DMSO solv. only | None | 1.00 | 2.0 ± 0.9 |
| Fla | 10 μM × 48 | " | 1.05 | 1.3 ± 0.7 |
| Fla | 20 μM × 48 | " | 0.93 | 1.0 ± 0.6 |
| Fla | 40 μM × 48 | " | 0.75 | 2.8 ± 1 |
| Fla | 50 μM × 48 | " | 0.67 | 3.2 ± 0.9 |
| Fla | 100 μM × 48 | " | 0.45 | 3.2 ± 1.3 |
| control | DMSO solv. only | BNF | 1.00 | 1.8 ± 0.7 |
| Fla | 40 μM × 48 | " | 0.70 | 3.7 ± 1.3 |
| CONTROL | DMSO solv. | None | 1.00 | 1.8 ± 0.3 |

TABLE 5-continued

Mutation of AHH-1 Cells by Indirect-Acting Mutagens

| MUTAGEN | Conc. × Time(hours) | INDUCTION | RELATIVE SURVIVAL | MUTANT FRACTION × $10^6$ MEAN ± STD.DEV. |
|---|---|---|---|---|
| | only | | | |
| 2AAF | 25 μM × 48 | " | 0.73 | 4.8 ± 1.2 |
| 2AAF | 50 μM × 48 | " | 0.50 | 3.8 ± 1.1 |
| 2AAF | 75 μM × 48 | " | 0.37 | 6.9 ± 1.7 |
| 2AAF | 100 μM × 48 | " | 0.33 | 7.7 ± 0.7 |
| control | DMSO solv. only | None | 1.00 | 0.7 ± 0.3 |
| Per | 10 μM × 48 | " | 0.93 | 3.2 ± 0.75 |
| Per | 20 μM × 48 | " | 0.95 | 1.9 ± 0.5 |
| control | DMSO solv. only | BNF | 1.00 | 2.8 ± 0.65 |
| Per | 10 μM × 48 | " | 0.89 | 2.7 ± 0.6 |
| Per | 20 μM × 48 | " | 0.89 | 2.7 ± 0.6 |

Example 8

Isolation of G6-A5

Another cell line, G6-A5, has been developed which exhibits properties similar to AHH-1. An initial screen was conducted in which 9 human cell lines were screened for the mixed function oxidative (MFO) activity and high plating efficiency (PE) which are characteristic of the AHH-1 cell line. The results of this screening are shown in Table 6.

TABLE 6

Summary of Characteristics of Cell Lines.

| Cell Line | MFO Act. Basal* | MFO Act. Induced* | Plating Eff. | EH (epoxide hydrolase) Act.** | PPLO (myco-plasma) |
|---|---|---|---|---|---|
| NC-37 | nd | nd | <0.001 | | neg |
| RPMI 1788 | nd | nd | 0.04 | | neg |
| RPMI 6666 | nd | nd | <0.001 | | neg |
| RPMI 7666 | 0.032 | 0.117 | <0.001 | 0.24 | neg |
| CCRF-HSB-2 | 0.021 | 0.159 | 0.04 | 0.52 | neg |
| CCRF-SB | 0.035 | 0.154 | 0.04 | | neg |
| AN-8 | 0.014 | 0.049 | <0.001 | 0.013 | neg |
| B-23-2 | 0.034 | 0.071 | <0.001 | 0.060 | pos |
| SN 1006 | 0.018 | 0.064 | <0.001 | 0.062 | pos | nd - not detectable
*pmole resorufin per million cells per minute from 7-ethoxyresorufin
**pmole Benzo (a) pyrene-4,5-diol per million cells per minute from Benzo (a) pyrene-4,5-oxide The CCRF-HSB-2 (ATCC Accession No. CCL 120.1) cell line demonstrated several desirable characteristics including the fact that it did not contain the mycoplasma contamination which was present in the progenitor to the AHH-1 cell line. The CCRF-HSB-2 cell line, however, had relatively low MFO activity and relatively low PE.

In order to develop a cell line which could be mutated to a statistically significant degree in the absence of exogenous oxidative enzyme activity when contacted with a chemical requiring activation by oxidative enzymes to become mutagenic, the CCRF-HSB-2 cell line was maintained in exponential growth for approximately 2 months. During this two month period, the doubling time of the cell population decreased from 35 hours to 28 hours. This step was performed because it is known that cells which are growing rapidly tend to have higher PE. Prolonged growth tends to select for cells which grow more rapidly. The cells were then plated in medium containing 0.3% agarose (Coffino et al., Science 167:186–188 (1970)). After an appropriate period of incubation, colonies were isolated and the cells propagated to a bulk culture. The agarose plating procedure is known to provide a more stringent selection for cells with high PE than the microtitre plating procedure described above in connection with the AHH-1 cell line.

A total of 32 colonies were isolated from over 100,000 cells plated in agarose. Of these 32, 21 grew sufficiently to permit analysis. These subclones fell into two classes based on MFO activity and PE. One class was identified which had high MFO activity and low PE, and a second class was identified which had low MFO activity and high PE.

Two subclones (designated G1 and G6) having high PE and low MFO activity were subjected to selection based upon resistance to the phototoxicity of benzo(ghi)perylene. This technique, which is described, for example, by Van Gurp and Hankinson (Cancer Res. 43:6031–6038 (1983)), is known to be an effective means for selecting cells which contain high levels of MFO activity.

TABLE 7

Properties of Promising Subclones

| Subclone | Plating Efficiency | 7ER Deethylase Basal (MFO) | Activity* Induced |
|---|---|---|---|
| G1-A1-14 | 0.44 | 0.10 | 0.62 |
| G1-A2-23 | 0.18 | 0.13 | 0.61 |
| G6-A5 | 0.69 | 0.11 | 0.76 |
| G6-A6 | 0.20 | 0.07 | 1.13 |
| G6-A7 | 0.36 | 0.02 | 0.19 |
| G6-20 | 0.32 | 0.04 | 0.28 |
| G6-21 | 0.19 | 0.07 | 0.43 |
| CCRF-HSB-2 (Parent) | 0.04 | 0.021 | 0.159 |

*activities in pmoles resolution per million cells per minutes.

Following the benzo(ghi)perylene selection and after plating in microtitre plates, colonies were isolated and analyzed for MFO activity and PE. As shown in Table 7, several subclones were identified which had the desired properties of good PE and good MFO activity. Several of these subclones were used to detect the mutagenic activity of benzo(a)pyrene, a chemical known to require oxidative metabolism for mutagenicity. Several of these subclones were found to be mutated to a statistically significant degree when exposed directly to this chemical. Mutagenicity data from one clone, G6-A5, is shown in Table 8.

TABLE 8

Mutagenicity Data for G6-A5 Clone

| Treatment | Relative Survival | Mutant Fraction HGPRT LOCUS (×10$^6$)* |
|---|---|---|
| Negative Control | 1.00 | 32 ± 1 |
| 0.1 μg/ml Benzo(a)pyrene* | 0.37 | 247 ± 71 |
| 0.2 μg/ml Benzo(a)pyrene** | 0.41 | 230 ± 38 |

*mean +/− standard deviation
**24 hour treatment

Industrial Applicability

The invention described herein has industrial applicability in determining whether an industrial pollutant or other substance or process has a mutagenic effect upon human cells. In addition, this invention may be used to assess, simplify and improve compounds and procedures that are used in conducting mutagenicity assays involving human cells.

Equivalents

Those skilled in the art will recognize, or be able to ascertain using no more than routine experimentation, many equivalents to the specific embodiments of the invention described herein. Such equivalents are intended to be encompassed by the claims which follow.

REFERENCES

1. See, e.g., W. G. Thilly et al, "Gene-Locus Mutation Assays in Diploid Human Lymphoblast Lines," p 331–364, in *Chemical Mutagens*, Vol. 6, F. J. de Ferres et al, ed; Plenum Publ. Co., New York (1980).
2. T. R. Skopek et al, "Isolation of a Human Lymphoblastoid Line Heteroxygous at the TK Locus," *Biochem. Biophys. Res. Comm.* 84: 411–416 (1978).
3. See, e.g., A. W. Hsie et al, "The Dose-Response Relationship for Ethyl Methane Sulfonate-Induced Mutations at the HGPRT Locus in Chinese Hamster Ovary Cells," *Somatic Cell Genetics* 1: 247–261 (1975).
4. See, e.g., C. F. Arlett et al, "Mutation to 8-azaguanine Resistance Induced by α- irradiation in a Chinese Hamster Cell Line," *Mutation Res.* 13: 59–65 (1971).
5. See notes 1 and 2, supra.
6. See, e.g., W. Szybalski, "Drug Sensitivity as a Genetic Marker for Human Cell Lines," *Univ. Mich. Med. Bull.* 28: 277–293 (1962); R. J. Albertini et al, "Detection and Quantification of X-ray-induced Mutation in Cultured, Diploid Human Biroblasts,: *Mutat. Res.* 18: 199–244 (1973); U.S. Pat. No. 4,066,510 (Thilly, 1978).
7. See, e.g., C. de Dure et al, "Distribution of Enzymes Between Subcellular Fractions in Animal Tissues," *Adv. Enzymol. Relat. Subj. Biochem.* 24: 291–358 (1962).
8. See,e.q., C. Walsh, *Enzymatic Reacting Mechanisms*, p 309 et seq.; W. H. Freeman & Co., San Francisco (1979); Y. Hayaishi, *Molecular Mechanisms of Oxygen Activation*, p. 215 et seq., Academic Press, New, York (1974).
9. See, e.g., A. R. Dahl et al, "Cytochrome P-450-Dependent Monooxygenases in Olfactory Epithelium of Dogs: Possible Role in Tumorigenicity," *Science* 216: 57–59 (1982).
10. H. J. Freedman et al, "AHH in a Stable human B-Lymphocyte Cell Line, RPMI-1788," *Cancer Res.* 39: 4605–4611 (1979).
11. See, e.g., *Stedman's Medical Dictionary*, 23rd edition, p 911, Williams & Wilkins, Baltimore, Md. (1976).
12. See note 1, supra.
13. E. E. Furth et al, *Anal. Biochem.* 110: 1–8 (1981) 14. See note 2, supra.
15. B. W. Penmen et al, "Perylene Is a More Potent Mutagen than BaP for S. Typhimurium," *Mutat. Res.* 77: 271–277 (1980).

We claim:

1. A method of determining the mutagenicity of a suspected mutagen, comprising the steps of:
   a. maintaining a culture of a human lymphoblastoid cell line which can be mutated in the absence of exogenous oxidative enzyme activity when contacted with a chemical requiring activation by oxidative enzymes to become mutagenic;
   b. exposing the culture to the suspected mutagen;
   c. growing the exposed human cells for a phenotypic stabilization period;
   d. detecting the numbers of mutant cells; and
   e. comparing the frequency of mutation of the exposed human lymphoblastoid cells to the frequency of mutation of unexposed control human lymphoblastoid cells to determine mutagenicity of the suspected mutagen.

2. A method of claim 1, wherein the suspected mutagen is a polynuclear aryl hydrocarbon.

3. A method of claim 2, wherein the suspected mutagen is aflatoxin $B_1$, benzo(α)-pyrene, 2-acetoaminofluorene or dimethylintrosamine.

4. An assay for assessing the mutagenicity of a suspected mutagen requiring metabolic activation by oxidative enzymes to become mutagenic, comprising the steps of:
   a. maintaining a culture of a human lymphoblastoid cell line which can be mutated in the absence of exogenous oxidative enzyme activity when contacted with a chemical requiring activation by oxidative enzymes to become mutagenic;
   b. exposing the culture to the suspected mutagen;
   c. growing the exposed human cells for a phenotypic stabilization period;
   d. detecting the numbers of mutant cells;
   e. comparing the frequency of mutation of the exposed human lymphoblastoid cells to the frequency of mutation of unexposed control human lymphoblastoid cells to determine the mutagenicity of the suspected mutagen.

5. A culture consisting essentially of a human lymphoblastoid cell line having the following characteristics:
   a. rapid growth rate and high cloning efficiency;
   b. absence of mycoplasma;
   c. capable of continuous reproduction in suspension culture; and
   d. ability to be mutated in the absence of exogenous oxidative acitivity if said culture is contacted with a chemical which is known to require oxidative activation in order to become capable of causing genetic change.

6. A culture consisting essentially of a human lynphoblastoid cell line capable of continuous reproduction in suspension culture, said human lymphoblastoid cell line possessing sufficient endogenous oxidative activity such that the cell line is mutated in the absence of exogenous oxidative enzymes when contacted with a chemical requiring activation by oxidative enzymes to become mutagenic.

7. A culture of claim 6, wherein the human lymphoblastoid cell line is homogenous.

8. A culture of claim 6, wherein the human lymphoblastoid cell line has a plating efficiency of about 40 to about 80 percent in RPMI medium 1640 supplemented with 5% by volume of blood serum.

9. A culture of claim 6, wherein the human lymphoblastoid cell line comprises cells which are not anchorage dependent.

10. A method of selecting human lymphoblastoid cells capable of being mutated in the absence of exogenous oxidative enzyme activity when contacted with a chemical requiring activation by oxidative enzymes to become mutagenic, comprising:

selecting a human lymphoblastoid cell line which contains some degree of AHH activity;

forming a plurality of cell colonies derived from the human lymphoblastoid cell line;

selecting the colonies which possess a high level of AHH activity;

exposing the cells from the selected colony to a known mutagen; and selecting cells which are suitable for use in a mutagenicity assay.

11. A method of claim 10, wherein the mutagen is a direct-acting mutagen.

12. A method of claim 10, wherein the human lymphoblastoid cell line in the first selecting step is RPMI-1788 cells.

13. A method of claim 10, wherein the human lymphoblastoid cell line in the first selecting step is decontaminated prior to the formation of a plurality of cell colonies.

* * * * *